(12) United States Patent
Aoyagi et al.

(10) Patent No.: US 7,345,761 B1
(45) Date of Patent: Mar. 18, 2008

(54) FILM MEASUREMENT

(75) Inventors: Paul Aoyagi, Sunnyvale, CA (US); Philip D. Flanner, III, Union City, CA (US); Leonid Poslavsky, Belmont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 305 days.

(21) Appl. No.: 10/945,166

(22) Filed: Sep. 20, 2004

(51) Int. Cl.
*G01J 4/00* (2006.01)

(52) U.S. Cl. .................................. 356/369; 356/630

(58) Field of Classification Search ................ 356/369, 356/630
See application file for complete search history.

(56) References Cited

U.S. PATENT DOCUMENTS

| | | | | |
|---|---|---|---|---|
| 4,999,014 A | * | 3/1991 | Gold et al. .................. | 356/632 |
| 5,121,337 A | * | 6/1992 | Brown ......................... | 702/28 |
| 6,782,337 B2 | * | 8/2004 | Wack et al. ................. | 702/155 |

OTHER PUBLICATIONS

Li, *Formulation and Comparison of Two Recursive Matrix Algorithms for Modeling Layered Diffraction Gratings*, J. Opt. Soc. Am. , vol. 13, No. 5, pp. 1024-1035 (1996).

Moharam et al., *Formulation for Stable and Efficient Implementation of the Rigorous Coupled-Wave Analysis of Binary Gratings*, Opt. Soc. Am. , vol. 12, No. 5, pp. 1068-1076 (1995).

* cited by examiner

*Primary Examiner*—Roy M. Punnoose
(74) *Attorney, Agent, or Firm*—Luedeka, Neely & Graham, P.C.

(57) ABSTRACT

A method of determining actual properties of layered media. An incident beam of light is directed towards the layered media, such that the incident beam of light is reflected from the layered media as a reflected beam of light. The actual properties of the reflected beam of light are measured, and properties of the layered media are estimated. A mathematical model of the layered media is solved with the estimated properties of the layered media to yield theoretical properties of the reflected beam of light. The mathematical model is solved using at least one of a modified T matrix algorithm and a Z matrix algorithm. The theoretical properties of the reflected beam of light are compared to the actual properties of the reflected beam of light to yield a cost function. The estimated properties of the layered media are iteratively adjusted and the mathematical model is iteratively solved until the cost function is within a desired tolerance. The estimated properties of the layered media are reported as the actual properties of the layered media.

20 Claims, 1 Drawing Sheet

FILM MEASUREMENT

FIELD

This invention relates to the field of film measurement. More particularly, this invention relates to a system for improving the speed and accuracy of multi layered film stack thickness measurement and other property measurement, such as in the integrated circuit fabrication industry.

BACKGROUND

As used herein, the term "integrated circuits" generally refers to monolithic semiconducting devices, such as those formed of group IV materials like silicon or germanium or mixtures thereof, or group III-V compounds such as gallium arsenide. The term "integrated circuits" includes all known configurations of such devices, such as memory and logic, and all designs of such devices, such as CMOS and bipolar.

Integrated circuits are formed of many layers of different materials, which layers are patterned so as to form desired structures that interact with one another according to predetermined designs. Thus, it is of vital importance that many of these layers be formed to very exacting tolerances, such as in their shape, thickness, and composition. If the various structures so formed during the integrated circuit fabrication process are not precisely formed, then the integrated circuit tends to not function in the intended manner, and may not function at all.

Because the layers of which integrated circuits are formed are so thin and patterned to be so small, they cannot be inspected without the aid of instrumentation. The precision of the instrumentation used is, therefore, vital to the successful production of integrated circuits. Thus, any improvement that can be made in the accuracy of such instrumentation is a boon to the integrated circuit fabrication industry. In addition, any improvement in the speed at which such instrumentation can take its readings is also of benefit to the industry, as such speed enhancements tend to reduce the production bottlenecks at inspection steps, or alternately allow for the inspection of a greater number of integrated circuits at such inspection steps.

Spectral ellipsometers and dual beam spectrophotometers are typically used to measure properties such as thickness and refractive index of individual layers within a multilayered film stack. Such instruments work by directing one or more beams of light toward the surface of the film stack, and then sensing the properties of the light as it is variously reflected off of the different surfaces of the individual layers within the film stack. By adjusting the properties of the incident beam of light, and detecting the associated changes in the reflected beam of light, the properties of the film stack, such as the materials of which the various layers are formed and thicknesses to which they are formed, can be determined.

This film measurement process can be broken down into two basic steps, being 1) the measurement of the properties of the reflected light beam, and 2) the mathematical fitting of computed reflectance property values based on some theoretical model, such as Rigorous Coupled Wave Analysis, to the measured results attained in step 1. Step 2 typically consists of the iterated steps of computing one or more theoretical value by plugging estimates of the film stack parameters, such as thickness and refractive index, into the model film stack equations, comparing the theoretical values obtained to the actual measured property values of the reflected beam of light, and if the theoretical values and the measured values do not agree to within a desired tolerance, then adjusting the estimated film stack parameters and recomputing the theoretical values.

This process is performed again and again, each time making some adjustment to the estimated film stack parameters that are fed into the model, until the theoretical values computed by the model agree with the actual measured values within the desired precision limits. When this agreement is attained, then there is some confidence that the estimated film stack parameters that were used to produce the theoretical values are very nearly the same as the actual film stack parameters.

For many film stacks, the step of iterative computing as described above consumes by far the most time during the process. For some film stacks, such as those film stacks that contain patterned lines, this iterative steps becomes extremely complex, because of the tremendous overhead of computing and tracking reflections at multiple diffracting angles.

The reflectance equations that are derived for film stacks that generate multiple plane waves traveling at different angles are typically-formulated using at least one of the S matrix algorithm or the R matrix algorithm, as understood by those with skill in the art. However, these algorithms are computationally burdensome, and require a longer than desirable period of time—and greater than desirable computational resources—to solve. Another well-known alternate formulation for computing the reflectance is the T matrix algorithm. Although this algorithm is more computationally efficient, it is highly susceptible to computational overflow error and is therefore seldom used in practical applications.

What is needed, therefore, is a method of spectral film stack measurement that tends to reduce at least some of the problems described above.

SUMMARY

The above and other needs are met by a method of determining actual properties of layered media. An incident beam of light is directed towards the layered media, such that the incident beam of light is reflected from the layered media as a reflected beam of light. The actual properties of the reflected beam of light are measured, and properties of the layered media are estimated. A mathematical model of the layered media is solved with the estimated properties of the layered media to yield theoretical properties of the reflected beam of light. The mathematical model is solved using at least one of a modified T matrix algorithm and a Z matrix algorithm. The theoretical properties of the reflected beam of light are compared to the actual properties of the reflected beam of light to yield a cost function. The estimated properties of the layered media are iteratively adjusted and the mathematical model is iteratively solved until the cost function is within a desired tolerance. The estimated properties of the layered media are reported as the actual properties of the layered media.

The embodiments of the present invention differ from the prior methods in that the S or R matrix algorithms are replaced with one of a more efficient modified T matrix or Z matrix algorithm—as described more completely herein—to compute the layered media reflectance. In this manner, the computational time and memory requirements are reduced. In particular, an operation count indicates that the Z matrix algorithm reduces the number of full matrix multiplications by about 40% to about 45%, in comparison to the S and R matrices, as well as significantly reducing the caching requirements needed for optimizing computation speed by eight full complex matrices per grating layer per wavelength. The modified T matrix reduces the number of full matrix multiplications by about 43% to about 48%, in comparison to the S and R matrices, as well as reducing the caching requirements needed for optimizing computation speed by six full complex matrices per grating layer per wavelength.

In various embodiments, the method is implemented in an ellipsometer. The layered media may be layers of more than one material, or more than one layer, or is a film stack on a semiconducting substrate, and preferably includes a grating layer. The actual properties of the layered media preferably include at least one of layer thickness and layer refractive index. In some embodiments the mathematical model is a reflectance model that is derived using rigorous coupled wave analysis. Preferably, the one of the Z matrix algorithm and the modified T matrix algorithm are used to compute a reflectance of the layered media. The method may also be implemented in a scatterometer. In various embodiments, at least one of the modified T matrix and the Z matrix is used in combination with at least one of an S matrix algorithm and an R matrix algorithm. This invention is preferably implemented as an add-in to existing instrument software.

According to another aspect of the invention there is described a method of determining a reflectance of a layered media by iteratively solving a mathematical model of the layered media with estimated properties of the layered media, where the mathematical model is solved using at least one of the modified T matrix algorithm and the Z matrix algorithm.

BRIEF DESCRIPTION OF THE DRAWINGS

Further advantages of the invention are apparent by reference to the detailed description when considered in conjunction with the FIGURE, which is not to scale so as to more clearly show the details, wherein like reference numbers indicate like elements, and wherein the figure is a representation of a film stack coordinate system.

DETAILED DESCRIPTION

Reflectance Calculation

Figure 1:
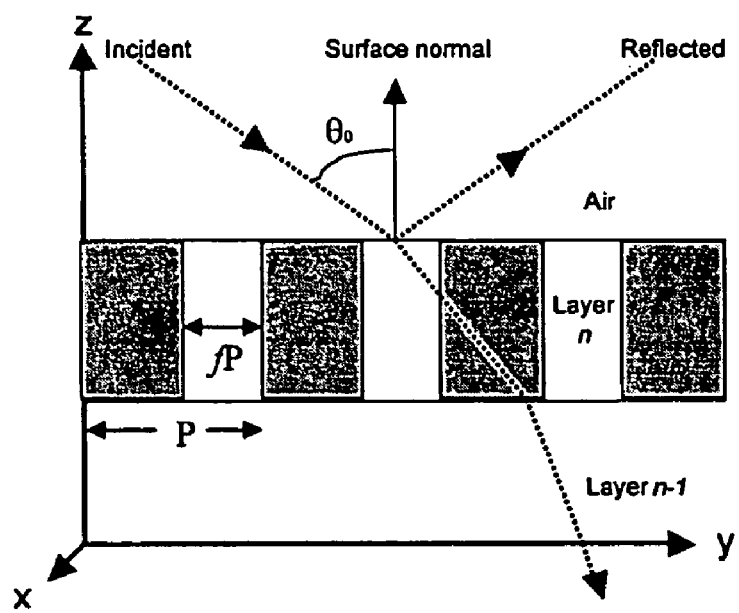

The fields at the top of the multiplayer film stack are related to the fields at the bottom by a product of propagation matrices for each layer. Pre- and post-multiplication by P matrices of the air and substrate transforms to an expression in terms of the incident amplitude $\tilde{A}$, the reflected amplitude $\tilde{R}$ the transmitted amplitude $\tilde{T}$, and three transformation matrices, X, P, and P', as:

$$\begin{bmatrix} \tilde{A} \\ \tilde{R} \end{bmatrix} = \frac{1}{2^{n+1}} P'_{air} P_n X_n P'_n \ldots P_1 X_1 P'_1 P_{substrate} \begin{bmatrix} T \\ 0 \end{bmatrix} \text{ where} \quad 1$$

$$P_j = \begin{bmatrix} P_{(1,1),j} & P_{(1,2),j} \\ P_{(2,1),j} & P_{(2,2),j} \end{bmatrix}, P'_j = \begin{bmatrix} P'_{(1,1),j} & P'_{(1,2),j} \\ P'_{(2,1),j} & P'_{(2,2),j} \end{bmatrix}$$

Preferably, only the relative reflectance and transmittance matrices R and T are computed, that relate the incident to reflected and transmitted amplitudes, $\tilde{R}=R\tilde{A}$ and $\tilde{T}=T\tilde{A}$. R and T are directly available if the matrix product is cast in the following form (with x indicating an element whose value is irrelevant):

$$\begin{bmatrix} \tilde{A} \\ \tilde{R} \end{bmatrix} = \begin{bmatrix} I & x \\ R & x \end{bmatrix}\begin{bmatrix} T^{-1} & 0 \\ 0 & x \end{bmatrix}\begin{bmatrix} \tilde{T} \\ 0 \end{bmatrix} = \begin{bmatrix} C\tilde{T} \\ RC\tilde{T} \end{bmatrix} \Rightarrow \begin{matrix} \tilde{A} = T^{-1}\tilde{T} \\ \tilde{R} = RT^{-1}\tilde{T} = R\tilde{A} \end{matrix} \quad 2$$

If a partial product in this form is multiplied by a full matrix G, the result is preferably recast into the same form:

$$\begin{bmatrix} \tilde{A} \\ \tilde{R} \end{bmatrix} = \ldots \begin{bmatrix} G_{11} & G_{12} \\ G_{21} & G_{22} \end{bmatrix}\begin{bmatrix} I & x \\ R & x \end{bmatrix}\begin{bmatrix} T^{-1} & 0 \\ 0 & x \end{bmatrix}\begin{bmatrix} \tilde{T} \\ 0 \end{bmatrix} \quad 3$$

$$= \ldots \begin{bmatrix} G_{11}+G_{12}R & x \\ G_{21}+G_{22}R & x \end{bmatrix}\begin{bmatrix} T^{-1} & 0 \\ 0 & x \end{bmatrix}\begin{bmatrix} \tilde{T} \\ 0 \end{bmatrix}$$

$$= \ldots \begin{bmatrix} I & x \\ (G_{21}+G_{22}R)(G_{11}+G_{12}R)^{-1} & x \end{bmatrix}$$

$$\begin{bmatrix} (T(G_{11}+G_{12}R)^{-1})^{-1} & 0 \\ 0 & x \end{bmatrix}\begin{bmatrix} \tilde{T} \\ 0 \end{bmatrix}$$

Thus multiplication by each matrix G in the product chain is equivalent to updating the R and T matrices according to:

$$R \leftarrow (G_{21}+G_{22}R)(G_{11}+G_{12}R)^{-1}$$

$$T \leftarrow T(G_{11}+G_{12}R)^{-1} \quad 4$$

There is preferably one such update for each of the three matrices in the field propagation solution.

Only the R update is preferably considered, as the present application preferably uses only reflectance. For each layer j, the update value at the layer bottom is called $R_{B,j}$, at the layer top $R_{T,j}$, and the fields at the interface $Z_j$ (at the layer bottom and top the update relates up/down traveling waves and is thus like a reflectance; at the interface it relates H to E fields and is like an admittance, at least for the TE case).

By identifying a correspondence between the elements in equations 1 and 3, equation 4 can be expressed as a Z matrix algorithm:

$$R_{B,j}=(P'_{(2,1),j}Z_{j-1}+P'_{(2,2),j})(P'_{(1,1),j}Z_{j-1}+P'_{(1,2),j})^{-1}$$

$$R_{T,j}=X_{(2,2),j}R_{B,j}X_{(1,1),j}^{-1}$$

$$Z_j=(P_{(1,1),j}+P_{(1,2),j}R_{T,j})(P_{(2,1),j}+P_{(2,2),j}R_{T,j})^{-1} \quad 5$$

The Z matrix algorithm in 5 can alternately be rewritten by factoring out $Z_{j-1}$ and rewriting in terms of the admittance matrix $Z_{j-1}=Y_{j-1}^{-1}$. This alternate Z matrix algorithm is given by:

$$R_{B,j}=(P'_{(2,1),j}+P'_{(2,2),j}Y_{j-1})(P'_{(1,1),j}+P'_{(1,2),j}Y_{j-1})^{-1}$$

$$R_{T,j}=X_{(2,2),j}R_{B,j}X_{(1,1),j}^{-1}$$

$$Y_j=(P_{(2,1),j}+P_{(2,2),j}R_{T,j})(P_{(1,1),j}+P_{(1,2),j}R_{T,j})^{-1} \quad 6$$

Alternately, a modified T matrix algorithm can be derived from equation 5 or 6 by eliminating explicit computation of Z or Y. The characteristic equations of the modified T matrix algorithm is given by:

$$R_{B,j}=(P'_{(2,1),j}(P_{(1,1),j-1}+P_{(1,2),j-1}R_{T,j-1})+P'_{(2,2),j}$$
$$(P_{(2,1),j-1}+P_{(2,2),j-1}R_{T,j-1})\times$$

$$(P'_{(1,1),j}(P_{(1,1),j-1}+P_{(1,2),j-1}R_{T,j-1})+P'_{(1,2),j}$$
$$(P_{(2,1),j-1}+P_{(2,2),j-1}R_{T,j-1}))^{-1}$$

$$R_{T,j}=X_{(2,2),j}R_{B,j}X_{(1,1),j}^{-1} \quad 7$$

The advantage of doing the modified T matrix formulation relative to the Z matrix formulation is the elimination of a computationally expensive matrix inversion. Conversely, the relative advantage of the Z matrix formulation over the modified T matrix formulation is that the reflectance computation at each layer reduces the dependence on parameters of the layer below it. Specifically, the $R_{B,j}$, $R_{T,j}$ as computed in the Z matrix formulation depends only on $Z_{j-1}$ whereas for the modified T matrix algorithm $R_{B,j}$, $R_{T,j}$ depend on $P_{j-1}$ and $R_{T,j-1}$. This reduced dependence results in less computer memory (caching) needed to achieve the same level of computational efficiency.

Detailed Example Using Rigorous Coupled Wave Analysis (RCWA)

Basic Equations—Rigorous Coupled Wave Analysis

Maxwell's equations are preferably the starting point for regions without sources (free charge or current):

$$\vec{\nabla} \times \vec{E} + \frac{1}{c}\frac{\partial \vec{B}}{\partial t} = 0$$
$$\vec{\nabla} \times \vec{H} - \frac{1}{c}\frac{\partial \vec{D}}{\partial t} = 0$$
$$\vec{\nabla} \cdot \vec{D} = 0$$
$$\vec{\nabla} \cdot \vec{B} = 0$$

(8)

and the material constitutive relations:

$$\overline{D} = \in \cdot \overline{E}$$
$$\overline{B} = \mu \cdot \overline{H}$$

where $\in$ and $\mu$ could in general be tensors for linear anisotropic materials, although the present discussion only considers materials that are non-magnetic with isotropic or uniaxial birefringent dielectric constant.

Combining the two curl equations for E and H with the constitutive relations gives:

$$\vec{\nabla} \times \vec{E} + \frac{\mu}{c} \cdot \frac{\partial \vec{H}}{\partial t} = 0$$
$$\vec{\nabla} \times \vec{H} - \frac{\varepsilon}{c} \cdot \frac{\partial \vec{E}}{\partial t} = 0$$

(10)

Note that the equations are unchanged under the transformation $E \leftrightarrow H$, $\in \leftrightarrow -\mu$.

Now the assumption of a monochromatic field is preferably made, with time dependence $e^{i\omega t} = e^{2\pi i c t/\lambda}$, and the time dependent part of the fields is dropped (for example, $E = \overline{E}e^{i\omega t}$):

$$\vec{\nabla} \times \vec{E} + \frac{2\pi i}{\lambda}\mu \cdot \vec{H} = 0$$
$$\vec{\nabla} \times \vec{H} - \frac{2\pi i}{\lambda}\varepsilon \cdot \vec{E} = 0$$

(11)

A wave equation is obtained by taking the curl of either equation and substituting the other into the result (using the identity $\vec{\nabla} \times (\vec{\nabla} \times E) = \vec{\nabla}(\vec{\nabla} \cdot E) - \nabla^2 E$ and defining $k_0 = 2\pi/\lambda$):

$$\vec{\nabla} \times (\vec{\nabla} \times \overline{E}) + ik_0 \mu \cdot \vec{\nabla} \times \overline{H} \Rightarrow \vec{\nabla}(\vec{\nabla} \cdot \overline{E}) - \nabla^2 \overline{E} - k_0^2 \mu \in \cdot \overline{E} \Rightarrow \nabla^2 \overline{E} + k_0^2 \mu \in \cdot \overline{E} = 0$$

(12)

Define $n^2 = \mu \in$ for the isotropic case, $$n^2 = \begin{pmatrix} n & 0 & 0 \\ 0 & n & 0 \\ 0 & 0 & n_z \end{pmatrix}^2 \equiv \begin{pmatrix} \mu\varepsilon & 0 & 0 \\ 0 & \mu\varepsilon & 0 \\ 0 & 0 & \mu_z\varepsilon_z \end{pmatrix}$$

for the uniaxial birefringence case, and $\overline{k} = k_0 n \cdot \hat{k}$ where $\hat{k}$ is for now an arbitrary unit vector. The general solution to equation 10 is then:

$$\overline{E}(\vec{r},t) = \overline{E}_0 e^{i\omega t - i\vec{k}\cdot\vec{r}} + \overline{E}_1 e^{i\omega t + i\vec{k}\cdot\vec{r}}$$

(13)

Film Stack

The film stack coordinate system is defined as shown in the FIGURE. Monochromatic light is incident from the air at top on the surface of layer n, making an angle $\theta_0$ with respect to the surface normal. One or more layers are assumed to be gratings, and all grating layers preferably have the same pitch P. Currently, gratings are preferably defined to consist of two materials, line and space, with dielectric constants $\in_L$ and $\in_S$. The width of the space material is defined by the space fraction f (the space width is fP and the line width (1−f)P). The grating lines are perpendicular to the plane of incidence (referred to as a grating azimuth angle of 0°), so that $\in$ is preferably a function of y only and the fields are preferably functions of y and z only.

Fourier Series Representation

In the Rigorous Coupled Wave Analysis method of solution, one-dimensional Fourier series representations are preferably used for the y dependence of the fields and the dielectric constant. In general, a periodic function F(y) in matrix-vector form is represented herein by a column vector F of the Fourier series coefficients $F_n$. The series and it's derivative are:

$$F(y) = \sum_{n=-\infty}^{\infty} F_n e^{2\pi i n y/P} \quad (F)$$

$$\frac{dF}{dy} = \sum_{n=-\infty}^{\infty} \frac{2\pi i n}{P} F_n e^{2\pi i n y/P} \quad \left(\frac{dF}{dy} = \Omega F, \Omega_{mn} = \begin{cases} \frac{2\pi i n}{P} = ik_0 \frac{n\lambda}{P} & (n=m) \\ 0 & (n \neq m) \end{cases}\right)$$

(14)

The convolution theorem is preferably used, being: the product $C(y)=\in(y)G(y)$ of two periodic functions (with the same period) has a Fourier series representation with coefficients $$C_n = \sum_m \varepsilon_{n-m} G_m.$$

In matrix form, $C=T_\in G$ where $T_\in$ is the Toeplitz convolution matrix:

$$T_\varepsilon = \begin{bmatrix} \varepsilon_0 & \varepsilon_{-1} & \varepsilon_{-2} & \varepsilon_{-3} & \cdots \\ \varepsilon_1 & \varepsilon_0 & \varepsilon_{-1} & \varepsilon_{-2} & \ddots \\ \varepsilon_2 & \varepsilon_1 & \varepsilon_0 & \varepsilon_{-1} & \ddots \\ \varepsilon_3 & \varepsilon_2 & \varepsilon_1 & \varepsilon_0 & \ddots \\ \vdots & \ddots & \ddots & \ddots & \ddots \end{bmatrix}$$

Dielectric Constant

The dielectric constant $\in(y)$ in the grating layer is preferably represented by a Fourier series with Toeplitz convolution matrix $T_\in$ (the inverse dielectric constant may also be used, in which case it is represented by $T_{1/\in}$). Taking y=0 to be at the center of the space region, the Fourier coefficients $\in_m$ are given by:

$$\varepsilon_m = \begin{cases} f(\varepsilon_S - \varepsilon_L) + \varepsilon_L & (m = 0) \\ f(\varepsilon_S - \varepsilon_L)\frac{\sin(\pi m f)}{\pi m f} & (m \neq 0) \end{cases} \quad 16$$

and similarly for the inverse dielectric constant:

$$\left(\frac{1}{\varepsilon}\right)_m = \begin{cases} f\left(\frac{1}{\varepsilon_S} - \frac{1}{\varepsilon_L}\right) + \frac{1}{\varepsilon_L} & (m = 0) \\ f\left(\frac{1}{\varepsilon_S} - \frac{1}{\varepsilon_L}\right)\frac{\sin(\pi m f)}{\pi m f} & (m \neq 0) \end{cases} \quad 17$$

The symmetry of the sine function implies the Toeplitz matrices are symmetric.

Field Solutions

TE Case

For the TE case, $E_y=E_z=H_x=0$. Expanding the curl equations 11 within one layer:

From $\vec{\nabla} \times \vec{H} - \frac{2\pi i}{\lambda}\varepsilon \cdot \vec{E} =$ 0: From $\vec{\nabla} \times \vec{E} + \frac{2\pi i}{\lambda}\mu \cdot \vec{H} = 0$:

$$\frac{\partial H_z}{\partial y} - \frac{\partial H_y}{\partial z} - ik_0\varepsilon E_x = 0 \quad H_x = 0 \quad 18a, b$$

$$\frac{\partial H_z}{\partial x} = 0 \quad \frac{\partial E_x}{\partial z} + ik_0\mu H_y = 0 \quad 19a, b$$

-continued $$\frac{\partial H_y}{\partial x} = 0 \quad -\frac{\partial E_x}{\partial y} + ik_0\mu_z H_z = 0 \quad 20a, b$$

The fields $E_x$, $H_y$, $H_z$ are preferably assumed to have the same periodicity and Fourier representation as $\in$, with the addition of a plane wave phase term:

$$E_x = \left(\sum_m E_{xm}(z)e^{2\pi i n y/P}\right)e^{-ik_0\alpha y} \quad (\alpha = n_{air}\sin\theta_0) \quad 21$$

The derivative of a field quantity with respect to y in matrix-vector form is then:

$$\frac{dE_x}{dy} = (\Omega - ik_0\alpha I)_x \equiv ik_0 K_x E_x \text{ where } K_{x;m,n} = \begin{cases} \frac{n\lambda}{P} - \alpha & (m-n) \\ 0 & (m \neq n) \end{cases} \quad 22$$

The curl equations 18a, 19b, and 20b in matrix-vector form are:

$$ik_0 K_x H_z - \frac{dH_y}{dz} - ik_0 T_\varepsilon E_x = 0 \quad 23$$

$$ik_0 T_\mu H_y = -\frac{dE_x}{dz}$$

$$T_{\mu_z} H_z = K_x E_x$$

The equations could be formed in terms of $T_{1/\in}$, for example, by dividing equation 18a through by $\in$ before converting to matrix-vector form.

Eliminating $H_y$ and $H_z$ gives a second order equation in $E_x$:

$$\frac{d^2 E_x}{dz^2} = k_0^2 T_\mu (K_x T_{\mu_z}^{-1} K_x - T_\varepsilon) E_x \equiv -k_0^2 S^2 E_x \quad 24$$

Assuming non-magnetic materials, the system matrix S for the TE case is given by:

$$S_{TE}^2 = T_\in - K_x^2 \quad (25)$$

The solutions of the second order differential equation 24 are the matrix exponential functions $e^{ik_0 Sz}$ and $e^{-ik_0 Sz}$, corresponding respectively to downward and upward traveling plane waves (because of the $e^{i\omega t}$ time dependence, assuming square root of $S^2$ is defined to yield positive real part). A complete solution in terms of both up and down plane waves given boundary conditions on $E_x$ and it's derivative at z=0 is:

$$E_x = \frac{1}{2}(e^{ik_0 Sz} + e^{-ik_0 Sz})E_{x0} + \frac{S^{-1}}{2ik_0}(e^{ik_0 Sz} - e^{-ik_0 Sz})E'_{x0} \quad 26$$

$$E'_x = \frac{ik_0 S}{2}(e^{ik_0 Sz} - e^{-ik_0 Sz})E_{x0} + \frac{1}{2}(e^{ik_0 Sz} + e^{-ik_0 Sz})E'_{x0}$$

This can be written in terms of the tangential field $-H_y$ since it is proportional to E'hd x(from (23), $ik_0 T_\mu(-H_y)=E'_x$):

$$E_x = \frac{1}{2}((e^{ik_0Sz} + e^{-ik_0Sz})E_{x0} + (e^{ik_0Sz} - e^{-ik_0Sz})S^{-1}T_\mu(-H_{y0})) \quad 27$$

$$-H_y = \frac{1}{2}(T_\mu^{-1}S(e^{ik_0Sz} - e^{-ik_0Sz})E_{x0} + T_\mu^{-1}S(e^{ik_0Sz} + e^{-ik_0Sz})S^{-1}T_\mu(-H_{y0}))$$

where use is made of the fact that a matrix S commutes with it's exponential to move $S^{-1}$ in the first equation and insert the term $SS^{-1}$ in the second, allowing the matrix form:

$$\begin{bmatrix} E_x \\ -H_y \end{bmatrix} = \quad 28$$

$$\frac{1}{2}\begin{bmatrix} (e^{ik_0Sz} + e^{-ik_0Sz}) & (e^{ik_0Sz} - e^{-ik_0Sz})S^{-1}T_\mu \\ T_\mu^{-1}S(e^{ik_0Sz} - e^{-ik_0Sz}) & T_\mu^{-1}S(e^{ik_0Sz} + e^{-ik_0Sz})S^{-1}T_\mu \end{bmatrix}\begin{bmatrix} E_{x0} \\ -H_{y0} \end{bmatrix}$$

to be factored as:

$$\begin{bmatrix} E_x \\ -H_y \end{bmatrix} = \frac{1}{2}\underbrace{\begin{bmatrix} I & I \\ T_\mu^{-1}S & -T_\mu^{-1}S \end{bmatrix}}_{P}\underbrace{\begin{bmatrix} e^{ik_0Sz} & 0 \\ 0 & e^{-ik_0Sz} \end{bmatrix}}_{X}\underbrace{\begin{bmatrix} I & S^{-1}T_\mu \\ I & -S^{-1}T_\mu \end{bmatrix}}_{P^{-1}}\begin{bmatrix} E_{x0} \\ -H_{y0} \end{bmatrix} \quad 29$$

This formulation has the simple interpretation that $P^{-1}$ transform tangential fields at the bottom interface to up/down traveling waves, X propagates the traveling wave solutions from the bottom of the layer to the top, and P transforms back to tangential fields at the top interface. Since the tangential field components are continuous at the interfaces, propagation through multiple layers is preferably accomplished by multiplying each layer's matrix triple product.

TM Case

For the TM case, the duality substitution $E \Leftrightarrow H$, $\in \Leftrightarrow -\mu$ is preferably used to transform the TE case. Now $H_y = H_z = E_x = 0$ and the dual of the curl equations 23 is:

$$ik_0K_xE_z - \frac{dE_y}{dz} + ik_0T_\mu H_x = 0 \quad 30$$

$$ik_0T_\varepsilon E_y = \frac{dH_x}{dz}$$

$$-T_{\varepsilon_z}E_z = K_xH_x$$

The second order differential equation 24 becomes:

$$\frac{d^2H_x}{dz^2} = k_0^2T_\in(K_xT_{\varepsilon_z}^{-1}K_x - T_\mu)H_x \equiv -k_0^2S^2H_x \quad 31$$

Assuming non-magnetic materials, the system matrix S for the TM case is given by:

$$S_{TM}^2 = T_\in(I - K_xT_{\in_I}^{-1}K_x) \quad 32$$

The TM form of the solution is identical to the TE case (except $E_y$ is proportional to $+H'_x$):

$$\begin{bmatrix} H_x \\ E_y \end{bmatrix} = \frac{1}{2}\underbrace{\begin{bmatrix} I & I \\ T_\varepsilon^{-1}S & -T_\varepsilon^{-1}S \end{bmatrix}}_{P}\underbrace{\begin{bmatrix} e^{ik_0Sz} & 0 \\ 0 & e^{-ik_0Sz} \end{bmatrix}}_{X}\underbrace{\begin{bmatrix} I & S^{-1}T_\varepsilon \\ I & -S^{-1}T_\varepsilon \end{bmatrix}}_{P^{-1}}\begin{bmatrix} H_{x0} \\ -E_{y0} \end{bmatrix} \quad 33$$

Alternate Form—Explicit Eigensystem Expansion

The square of the system matrix ($S^2$) is readily computed from film stack model parameters, but it is S, it's inverse, and it's exponential that appear in the solution. All of these quantities are preferably computed given the eigensystem expansion $S^2 = WK_z^2W^{-1}$ (since $K_z^2$ is diagonal $K_z$, $e^{ik_0K_zz}$ and $K_z^{-1}$ are trivial to compute). Substituting the expansion into the TE field solution and canceling factors of $WW^{-1}$ where possible gives an alternate TE solution form:

$$\begin{bmatrix} E_x \\ -H_y \end{bmatrix} = \frac{1}{2}\begin{bmatrix} W & W \\ T_\mu^{-1}WK_z & -T_\mu^{-1}WK_z \end{bmatrix}\begin{bmatrix} e^{ik_0Sz} & 0 \\ 0 & e^{-ik_0Sz} \end{bmatrix}\begin{bmatrix} W^{-1} & K_z^{-1}W^{-1}T_\mu \\ W^{-1} & -K_z^{-1}W^{-1}T_\mu \end{bmatrix}\begin{bmatrix} E_{x0} \\ -H_{y0} \end{bmatrix} \quad 34$$

It is noted that this form is nearly the same as equation 29 with the S in the exponential terms replaced with $K_z$ and S outside the exponential replaced with $WK_z$. The additional occurrence of W and it's inverse are preferably factored out as follows:

$$\begin{bmatrix} E_x \\ -H_y \end{bmatrix} = \frac{1}{2}\begin{bmatrix} W & 0 \\ 0 & I \end{bmatrix}\begin{bmatrix} I & I \\ T_\mu^{-1}WK_z & -T_\mu^{-1}WK_z \end{bmatrix}\cdots\begin{bmatrix} W^{-1} & 0 \\ 0 & I \end{bmatrix}\begin{bmatrix} E_{x0} \\ -H_{y0} \end{bmatrix} \quad 35$$

Applying the result of equation 6 to the RCWA derived matrices in equation 29 gives for the TE updates (with $d_j$ as the thickness of layer j):

$$R_{B,j} = (I - S_j^{-1}T_{\mu,j}Y_{j-1})(I + S_j^{-1}T_{\mu,j}Y_{j-1})^{-1}$$

$$R_{T,j} = e^{-ik_0S_jd_j}R_{B,j}e^{-ik_0S_jd_j}$$

$$Y_j = T_{\mu,j}^{-1}S_j(I - R_{T,j})(I + R_{T,j})^{-1} \quad 36$$

The updates are preferably simplified by factoring out $Y_{j-1}$ and rewriting in terms of the impedance matrix $Z_{j-1} = Y_{j-1}^{-1}$.

$$R_{B,j} = (Z_{j-1} - S_j^{-1} T_{\mu,j})(Z_{j-1} + S_j^{-1} T_{\mu,j})^{-1}$$

$$R_{T,j} = e^{-ik_0 S_j d_j} R_{B,j} e^{-ik_0 S_j d_j}$$

$$Z_j = (I + R_{T,j})(I - R_{T,j})^{-1} S_j^{-1} T_{\mu,j} \qquad 37$$

The eigensystem expanded form is preferably made using the substitutions suggested below 35. The additional matrices with W and its inverse yield trivial updates which are preferably absorbed into Y (or Z):

$$\tilde{R}_{B,j} = (W_j^{-1} Z_{j-1} - K_{z,j}^{-1} W_j^{-1} T_{\mu,j})(W_j^{-1} Z_{j-1} + K_{z,j}^{-1} W_j^{-1} T_{\mu,j})^{-1}$$

$$\tilde{R}_{T,j} = e^{-ik_0 K_{z,j} d_j} \tilde{R}_{B,j} e^{-ik_0 K_{z,j} d_j}$$

$$Z_j = W_j(I + \tilde{R}_{T,j})(I - \tilde{R}_{T,j})^{-1} K_{z,j}^{-1} W_j^{-1} T_{\mu,j} \qquad 38$$

The intermediate reflectance quantities in the expanded form are not the same as in the previous equations, and are preferably converted if the true reflectance is required:

$$R_{B,j} = W_j \tilde{R}_{B,j} W_j^{-1}$$

$$R_{T,j} = W_j \tilde{R}_{T,j} W_j^{-1} \qquad 39$$

The expanded form of the update requires fewer operations to compute when the true reflectance is not needed, because the expanded form exponentials are diagonal matrices.

Calculation of the reflectance for the entire film stack preferably starts at the substrate (layer 0) where by definition $R_{T,0} = 0$ and $Y_0 = T_{\mu,0}^{-1} S_0$ ($Z_0 = S_0^{-1} T_{\mu,0}$), and preferably ends with the calculation of $R_{B,n+1}$ in the air above the stack (if there is surface roughness at the top layer, then $R_{T,n+1}$ is preferably computed).

Truncation to Finite Order

All of the matrix/vector quantities are of infinite dimension, with indices running from $-\infty$ to $+\infty$ corresponding to the indices of the defining Fourier series coefficients. In practice the series is preferably truncated, most preferably to a relatively small number of terms. The problem is truncated to order N when the E and H field Fourier coefficients $-N$ are kept to $+N$, for example, $2N+1$ total coefficients. It has been determined that the truncated problem tends to converge best with small N when the $\in$ convolution matrix $T_{1/\in}$ is used in the TM reflectance updates and the system matrices are computed as: $S_{TE}^2 = T_\in - K_x^2$ $$S_{TM}^2 = T_{1/\in_z}^{-1}(I - K_x T_\in^{-1} K_x) \qquad 40$$

CONCLUSION

The calculation of the film stack reflectance is preferably iterative, preferably starting at the substrate (layer 0) with the condition that $R_{T,0} = 0$ and proceeding through each layer until $R_{T,n+1}$ is computed. In non-grating layers, the dielectric constant Toeplitz matrices, and therefore the system matrices, are diagonal. This implies that beginning with the substrate, all computations are done with diagonal matrices until the first grating layer is reached.

The TE and TM polarization calculations preferably share common definition for the dielectric constant Toeplitz matrices and therefore $K_x$, but otherwise are preferably independent, although they share virtually the same form. In the following table the sequence of calculations for both polarizations are summarized, assuming non-magnetic materials:

| TE polarization | TM polarization |
|---|---|
| $S_{TE,j}^2 = T_{\in,j} - K_{x,j}^2$ | $S_{TM,j}^2 = T_{1/\in,j}^{-1}(I - K_{x,j} T_{\in,j}^{-1} K_{x,j})$ |
| $Z_0 = S_0^{-1}$ | $Z_0 = S_0^{-1} T_{1/\in,0}^{-1}$ |
| $R_{B,j} = (Z_{j-1} - S_j^{-1})(Z_{j-1} + S_j^{-1})^{-1}$ | $R_{B,j} = (Z_{j-1} - S_j^{-1} T_{1/\in,j}^{-1})(Z_{j-1} + S_j^{-1} T_{1/\in,j}^{-1})^{-1}$ |
| $R_{T,j} = e^{-ik_0 S_j d_j} R_{B,j} e^{-ik_0 S_j d_j}$ | $R_{T,j} = e^{-ik_0 S_j d_j} R_{B,j} e^{-ik_0 S_j d_j}$ |
| $Z_j = (I + R_{T,j})(I - R_{T,j})^{-1} S_j^{-1}$ | $Z_j = (I + R_{T,j})(I - R_{T,j})^{-1} S_j^{-1} T_{1/\in,j}^{-1}$ |

In expanded form, with the addition of a precomputed common sub-expression V, the TE and TM expressions preferably have identical form:

| TE polarization | TM polarization |
|---|---|
| $S_{TE,j}^2 = T_{\in,j} - K_{x,j}^2$ | $S_{TM,j}^2 = T_{1/\in,j}^{-1}(I - K_{x,j} T_{\in,j}^{-1} K_{x,j})$ |
| $Z_0 = S_0^{-1}$ | $Z_0 = S_0^{-1} T_{1/\in,0}^{-1}$ |
| $V_j = K_{z,j}^{-1} W_j^{-1}$ | $V_j = K_{z,j}^{-1} W_j^{-1} T_{1/\in,j}^{-1}$ |
| $\tilde{R}_{B,j} = (W_j^{-1} Z_{j-1} - V_j)(W_j^{-1} Z_{j-1} + V_j)^{-1}$ | $\tilde{R}_{B,j} = (W_j^{-1} Z_{j-1} - V_j)(W_j^{-1} Z_{j-1} + V_j)^{-1}$ |
| $\tilde{R}_{T,j} = e^{-ik_0 K_{z,j} d_j} \tilde{R}_{B,j} e^{-ik_0 K_{z,j} d_j}$ | $\tilde{R}_{T,j} = e^{-ik_0 K_{z,j} d_j} \tilde{R}_{B,j} e^{-ik_0 K_{z,j} d_j}$ |
| $Z_j = W_j(I + \tilde{R}_{T,j})(I - \tilde{R}_{T,j})^{-1} V_j$ | $Z_j = W_j(I + \tilde{R}_{T,j})(I - \tilde{R}_{T,j})^{-1} V_j$ |

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of determining actual properties of layered media, the method comprising the steps of:
    directing an incident beam of light towards the layered media, such that the incident beam of light is reflected from the layered media as a reflected beam of light,
    measuring actual properties of the reflected beam of light,
    estimating properties of the layered media,
    solving a mathematical model of the layered media with the estimated properties of the layered media to yield theoretical properties of the reflected beam of light, where the mathematical model is solved using at least one of a modified T matrix algorithm and a Z matrix algorithm,
    comparing the theoretical properties of the reflected beam of light to the actual properties of the reflected beam of light to yield a cost function,
    iteratively adjusting the estimated properties of the layered media and solving the mathematical model until the cost function is within a desired tolerance, and
    reporting the estimated properties of the layered media as the actual properties of the layered media.

2. The method of claim 1, wherein the method is implemented in an ellipsometer.

3. The method of claim 1, wherein the layered media comprises layers of more than one material.

4. The method of claim 1, wherein the layered media comprises more than one layer.

5. The method of claim 1, wherein the layered media includes a grating layer.

6. The method of claim 1, wherein the actual properties of the layered media include at least one of layer thickness and layer refractive index.

7. The method of claim 1, wherein the mathematical model is computationally solved at least partially using a Z matrix algorithm.

8. The method of claim 1, wherein the mathematical model is computationally solved at least partially using a modified T matrix algorithm.

9. The method of claim 1, wherein the mathematical model is a reflectance model that is derived using rigorous coupled wave analysis.

10. The method of claim 1, wherein the one of the Z matrix algorithm and the modified T matrix algorithm are used to compute a reflectance of the layered media.

11. The method of claim 1, wherein the method is implemented in a scatterometer.

12. The method of claim 1, wherein the layered media comprises a film stack on a semiconducting substrate.

13. The method of claim 1, wherein the modified T matrix is used in combination with at least one of an S matrix algorithm and an R matrix algorithm.

14. The method of claim 1, wherein the Z matrix is used in combination with at least one of an S matrix algorithm and an R matrix algorithm.

15. The method of claim 1, wherein the modified T matrix algorithm is characterized by:

$$R_{B,j}=(P'_{(2,1),j}(P_{(1,1),j-1}+P_{(1,2),j-1}R_{T,j-1})+P'_{(2,2),j}(P_{(2,1),j-1}+P_{(2,2),j-1}R_{T,j-1}))\times$$

$$(P'_{(1,1),j}(P_{(1,1),j-1}+P_{(1,2),j-1}R_{T,j-1})+P'_{(1,2),j}(T_{(2,1),j-1}+P_{(2,2),j-1}R_{T,j-1}))^{-1}$$

$$R_{T,j}=S_{(2,2),j}R_{B,j}X_{(1,1),j}^{-1}.$$

16. The method of claim 1, wherein the Z matrix algorithm is characterized by:

$$R_{B,j}(P'_{(2,1),j}Z_{j-1}+P'_{(2,2),j})(P'_{(1,1),j}Z_{j-1}+P'_{(1,2),j})^{-1}$$

$$R_{T,j}=X_{(2,2),j}R_{B,j}X_{(1,1),j}^{-1}$$

$$Z_j=(P_{(1,1),j}+P_{(1,2),j}R_{T,j})(P_{(2,1),j}+P_{(2,2),j}R_{T,j})^{-1}.$$

17. A method of determining a reflectance of a layered media by iteratively solving a mathematical model of the layered media with estimated properties of the layered media, where the mathematical model is solved using at least one of a modified T matrix algorithm and a Z matrix algorithm, producing a reflectance value indicative of the reflectance of the layered media.

18. The method of claim 17, wherein the method is implemented in an ellipsometer.

19. A method of determining actual properties of layered media having more than one layer and layers of more than one material and including a grating layer on a semiconducting substrate, the method comprising the steps of:
    directing an incident beam of light towards the layered media, such that the incident beam of light is reflected from the layered media as a reflected beam of light,
    measuring actual properties of the reflected beam of light, including at least one of layer thickness and layer refractive index,
    estimating properties of the layered media,
    solving a mathematical model of the layered media with the estimated properties of the layered media to yield theoretical properties of the reflected beam of light, where the mathematical model is solved using at least one of a modified T matrix algorithm and a Z matrix algorithm, wherein the mathematical model is a reflectance model that is derived using rigorous coupled wave analysis,
    comparing the theoretical properties of the reflected beam of light to the actual properties of the reflected beam of light to yield a cost function,
    iteratively adjusting the estimated properties of the layered media and solving the mathematical model until the cost function is within a desired tolerance, and
    reporting the estimated properties of the layered media as the actual properties of the layered media.

20. The method of claim 19, wherein the method is implemented in an ellipsometer.

* * * * *